United States Patent
Minkoff

(10) Patent No.: US 9,730,610 B1
(45) Date of Patent: Aug. 15, 2017

(54) MAGNETIC RESONANCE IMAGING OF THE SPINE TO DETECT SCOLIOSIS

(71) Applicant: Fonar Corporation, Melville, NY (US)

(72) Inventor: Lawrence A. Minkoff, Lattingtown, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 15/196,822

(22) Filed: Jun. 29, 2016

Related U.S. Application Data

(62) Division of application No. 12/152,139, filed on May 12, 2008, now Pat. No. 9,386,939.

(60) Provisional application No. 60/928,545, filed on May 10, 2007.

(51) Int. Cl.
| | |
|---|---|
| *A61B 5/055* | (2006.01) |
| *A61B 5/00* | (2006.01) |
| *G01R 33/3415* | (2006.01) |
| *G01R 33/36* | (2006.01) |
| *G01R 33/563* | (2006.01) |

(52) U.S. Cl.
CPC .......... *A61B 5/0555* (2013.01); *A61B 5/4561* (2013.01); *A61B 5/4566* (2013.01); *G01R 33/3415* (2013.01); *G01R 33/3642* (2013.01); *G01R 33/56383* (2013.01)

(58) Field of Classification Search
CPC ... A61B 5/0555; A61B 5/4561; A61B 5/4566; G01R 33/3415; G01R 33/3642; G01R 33/56383
See application file for complete search history.

(56) References Cited

U.S. PATENT DOCUMENTS

| | | | |
|---|---|---|---|
| 3,810,254 | A | 5/1974 | Utsumi et al. |
| 4,407,292 | A | 10/1983 | Edrich |
| 4,411,270 | A | 10/1983 | Damadian |
| 4,534,076 | A | 8/1985 | Barge |

(Continued)

FOREIGN PATENT DOCUMENTS

| | | |
|---|---|---|
| DE | 3140225 A1 | 4/1983 |
| JP | 1242056 | 9/1989 |

(Continued)

OTHER PUBLICATIONS

"The design and construction of high field-uniformity permanent magnet system for MRI" Feng, Z.X.; Jiang, X.H.;Han, S.; Magnetics, IEEE Transactions on vol. 28, Issue 1, Jan. 1992 pp. 641-643.

(Continued)

*Primary Examiner* — Bo J Peng
(74) *Attorney, Agent, or Firm* — Lerner, David, Littenberg, Krumholz & Mentlik, LLP

(57) ABSTRACT

In one aspect, the present invention is a method for detecting spinal abnormalities using magnet resonance imaging. The method comprises positioning a patient in an upright posture in an imaging volume of a magnet resonance imaging magnet with the spine of the patient adjacent to an antenna and capturing magnetic resonance imaging signals from a first portion of the patient's spine using the antenna with the patient positioned in a first position. The method may further comprise adjusting the patient position along a substantially vertical direction to a second position and capturing magnetic resonance imaging signals from a second portion of the patient's spine using the antenna with the patient positioned in the second position.

9 Claims, 7 Drawing Sheets

(56) References Cited

U.S. PATENT DOCUMENTS

| | | |
|---|---|---|
| 4,534,358 A | 8/1985 | Young |
| D283,858 S | 5/1986 | Opsvik |
| 4,608,991 A | 9/1986 | Rollwitz |
| 4,613,820 A | 9/1986 | Edelstein et al. |
| 4,614,378 A | 9/1986 | Picou |
| 4,629,989 A | 12/1986 | Riehl et al. |
| 4,641,119 A | 2/1987 | Moore |
| 4,651,099 A | 3/1987 | Vinegar et al. |
| 4,663,592 A | 5/1987 | Yamaguchi et al. |
| 4,664,275 A | 5/1987 | Kasai et al. |
| 4,668,915 A | 5/1987 | Daubin et al. |
| 4,672,346 A | 6/1987 | Miyamoto et al. |
| 4,675,609 A | 6/1987 | Danby et al. |
| 4,679,022 A | 7/1987 | Miyamoto et al. |
| 4,707,663 A | 11/1987 | Minkoff et al. |
| 4,766,378 A | 8/1988 | Danby et al. |
| 4,767,160 A | 8/1988 | Mengshoel et al. |
| 4,770,182 A | 9/1988 | Damadian et al. |
| 4,777,464 A | 10/1988 | Takabatashi et al. |
| 4,816,765 A | 3/1989 | Boskamp |
| 4,825,162 A | 4/1989 | Roemer et al. |
| 4,829,252 A | 5/1989 | Kaufman |
| 4,866,387 A | 9/1989 | Hyde et al. |
| 4,875,485 A | 10/1989 | Matsutani |
| 4,908,844 A | 3/1990 | Hasegawa |
| 4,918,388 A | 4/1990 | Mehdizadeh et al. |
| 4,920,318 A | 4/1990 | Misic et al. |
| 4,924,198 A | 5/1990 | Laskaris |
| 4,943,774 A | 7/1990 | Breneman et al. |
| 4,968,937 A | 11/1990 | Akgun |
| 4,975,644 A | 12/1990 | Fox |
| 4,985,678 A | 1/1991 | Gangarosa et al. |
| 5,008,624 A | 4/1991 | Yoshida |
| 5,030,915 A | 7/1991 | Boskamp et al. |
| 5,050,605 A | 9/1991 | Eydelman et al. |
| 5,061,897 A | 10/1991 | Danby et al. |
| 5,062,415 A | 11/1991 | Weatherby et al. |
| 5,065,701 A | 11/1991 | Punt |
| 5,065,761 A | 11/1991 | Pell |
| 5,081,665 A | 1/1992 | Kostich |
| 5,124,651 A | 6/1992 | Danby et al. |
| 5,134,374 A | 7/1992 | Breneman et al. |
| 5,153,517 A | 10/1992 | Oppelt et al. |
| 5,153,546 A | 10/1992 | Laskaris |
| 5,155,758 A | 10/1992 | Vogl |
| 5,162,768 A | 11/1992 | McDougall et al. |
| 5,171,296 A | 12/1992 | Herman |
| 5,194,810 A | 3/1993 | Breneman et al. |
| 5,197,474 A | 3/1993 | Englund et al. |
| 5,207,224 A | 5/1993 | Dickinson et al. |
| 5,221,165 A | 6/1993 | Goszczynski |
| 5,221,902 A | 6/1993 | Jones et al. |
| 5,229,723 A | 7/1993 | Sakurai et al. |
| 5,250,901 A | 10/1993 | Kaufman et al. |
| 5,251,961 A | 10/1993 | Pass |
| 5,256,971 A | 10/1993 | Boskamp |
| 5,274,332 A | 12/1993 | Jaskolski et al. |
| 5,291,890 A | 3/1994 | Cline et al. |
| 5,304,932 A | 4/1994 | Carlson |
| 5,305,365 A | 4/1994 | Coe |
| 5,305,749 A | 4/1994 | Li et al. |
| 5,305,750 A | 4/1994 | Makita |
| 5,315,244 A | 5/1994 | Griebeler |
| 5,315,276 A | 5/1994 | Huson et al. |
| 5,317,297 A | 5/1994 | Kaufman et al. |
| 5,323,113 A | 6/1994 | Cory et al. |
| 5,349,956 A | 9/1994 | Bonutti |
| 5,382,904 A | 1/1995 | Pissanetzky |
| 5,382,905 A | 1/1995 | Miyata et al. |
| 5,386,447 A | 1/1995 | Siczek |
| 5,394,087 A | 2/1995 | Molyneaux |
| 5,412,363 A | 5/1995 | Breneman et al. |
| 5,436,607 A | 7/1995 | Chari et al. |
| 5,471,142 A | 11/1995 | Wang |
| 5,473,251 A | 12/1995 | Mori |
| 5,475,885 A | 12/1995 | Ishikawa |
| 5,477,146 A | 12/1995 | Jones |
| 5,490,513 A | 2/1996 | Damadian et al. |
| 5,515,863 A | 5/1996 | Damadian |
| 5,519,372 A | 5/1996 | Palkovich et al. |
| 5,548,218 A | 8/1996 | Lu |
| 5,553,777 A | 9/1996 | Lampe |
| 5,566,681 A | 10/1996 | Manwaring et al. |
| 5,578,925 A | 11/1996 | Molyneaux et al. |
| 5,592,090 A | 1/1997 | Pissanetzky |
| 5,606,970 A | 3/1997 | Damadian |
| 5,621,323 A | 4/1997 | Larsen |
| 5,623,241 A | 4/1997 | Minkoff |
| 5,640,958 A | 6/1997 | Bonutti |
| 5,652,517 A | 7/1997 | Maki et al. |
| 5,654,603 A | 8/1997 | Sung et al. |
| 5,666,056 A | 9/1997 | Cuppen |
| 5,671,526 A | 9/1997 | Merlano |
| 5,680,861 A | 10/1997 | Rohling |
| 5,682,098 A | 10/1997 | Vij |
| 5,735,278 A | 4/1998 | Hoult et al. |
| 5,743,264 A | 4/1998 | Bonutti |
| 5,754,085 A | 5/1998 | Danby et al. |
| 5,779,637 A | 7/1998 | Palkovich et al. |
| 5,836,878 A | 11/1998 | Mock et al. |
| 5,862,579 A | 1/1999 | Blumberg |
| 5,929,639 A | 7/1999 | Doty |
| 5,951,474 A | 9/1999 | Matsunaga et al. |
| D417,085 S | 11/1999 | Kanwetz, II |
| 5,983,424 A | 11/1999 | Naslund |
| 5,988,173 A | 11/1999 | Scruggs |
| 6,008,649 A | 12/1999 | Boskamp et al. |
| 6,011,396 A | 1/2000 | Eckels et al. |
| 6,014,070 A | 1/2000 | Danby et al. |
| 6,023,165 A | 2/2000 | Damadian et al. |
| 6,029,082 A | 2/2000 | Srinivasan et al. |
| 6,075,364 A | 6/2000 | Damadian et al. |
| 6,122,541 A | 9/2000 | Cosman et al. |
| 6,137,291 A | 10/2000 | Szumowski et al. |
| 6,138,302 A | 10/2000 | Sashin et al. |
| 6,141,579 A | 10/2000 | Bonutti |
| 6,144,204 A | 11/2000 | Sementchenko |
| 6,150,819 A | 11/2000 | Laskaris et al. |
| 6,150,820 A | 11/2000 | Damadian et al. |
| 6,201,394 B1 | 3/2001 | Danby et al. |
| 6,208,144 B1 | 3/2001 | McGinley et al. |
| 6,226,856 B1 | 5/2001 | Kazama et al. |
| 6,246,239 B1 | 6/2001 | Krogmann et al. |
| 6,246,900 B1 | 6/2001 | Cosman et al. |
| 6,249,121 B1 | 6/2001 | Boskamp et al. |
| 6,249,695 B1 | 6/2001 | Damadian |
| 6,285,188 B1 | 9/2001 | Sakakura |
| 6,346,814 B1 | 2/2002 | Carrozzi et al. |
| 6,357,066 B1 | 3/2002 | Pierce |
| 6,369,571 B1 | 4/2002 | Damadian et al. |
| 6,377,044 B1 | 4/2002 | Burl et al. |
| 6,385,481 B2 | 5/2002 | Nose et al. |
| 6,411,088 B1 | 6/2002 | Kuth et al. |
| 6,414,490 B1 | 7/2002 | Damadian et al. |
| 6,424,854 B2 | 7/2002 | Hayashi et al. |
| 6,456,075 B1 | 9/2002 | Damadian et al. |
| 6,504,371 B1 | 1/2003 | Damadian et al. |
| 6,549,800 B1 | 4/2003 | Atalar et al. |
| 6,591,128 B1 | 7/2003 | Wu et al. |
| 6,608,917 B1 | 8/2003 | Wei et al. |
| 6,639,406 B1 | 10/2003 | Boskamp et al. |
| 6,656,143 B2 | 12/2003 | Browd |
| 6,677,753 B1 | 1/2004 | Danby et al. |
| 6,792,257 B2 | 9/2004 | Rabe |
| 6,801,038 B2 | 10/2004 | Carrozzi et al. |
| 6,806,711 B2 | 10/2004 | Reykowski |
| 6,850,064 B1 | 2/2005 | Srinivasan |
| 6,850,067 B1 | 2/2005 | Burl et al. |
| 6,882,149 B2 | 4/2005 | Nitz |
| 6,882,877 B2 | 4/2005 | Bonutti |
| 6,894,495 B2 | 5/2005 | Kan |
| 6,954,069 B2 | 10/2005 | Harvey et al. |
| 6,975,115 B1 | 12/2005 | Fujita et al. |
| 6,980,002 B1 | 12/2005 | Petropoulos et al. |

(56) References Cited

U.S. PATENT DOCUMENTS

| | | |
|---|---|---|
| 7,046,006 B2 | 5/2006 | Creemers |
| 7,049,819 B2 | 5/2006 | Chan et al. |
| 7,123,008 B1 | 10/2006 | Damadian et al. |
| 7,221,161 B2 | 5/2007 | Fujita et al. |
| 7,245,127 B2 | 7/2007 | Feng et al. |
| 7,348,778 B2 | 3/2008 | Chu et al. |
| 7,450,985 B2 | 11/2008 | Meloy |
| 7,474,098 B2 | 1/2009 | King |
| 7,551,954 B2 | 6/2009 | Green et al. |
| 7,680,525 B1 | 3/2010 | Damadian et al. |
| 7,701,209 B1 | 4/2010 | Green |
| 7,835,497 B2 | 11/2010 | Haras |
| 8,055,326 B1 | 11/2011 | Dworkin et al. |
| 9,138,164 B2 | 9/2015 | Driemel |
| 2001/0029330 A1 | 10/2001 | Nose et al. |
| 2002/0013524 A1 | 1/2002 | Hayashi et al. |
| 2002/0021128 A1 | 2/2002 | Kuhara |
| 2002/0032927 A1 | 3/2002 | Dinkler |
| 2002/0101241 A1 | 8/2002 | Chui |
| 2002/0123681 A1 | 9/2002 | Zuk et al. |
| 2002/0196021 A1 | 12/2002 | Wang |
| 2003/0026469 A1 | 2/2003 | Kreang-Arekul et al. |
| 2003/0059476 A1 | 3/2003 | Wang |
| 2003/0210049 A1 | 11/2003 | Boskamp et al. |
| 2003/0214301 A1 | 11/2003 | Lee |
| 2005/0020945 A1 | 1/2005 | Tosaya et al. |
| 2005/0122343 A1 | 6/2005 | Bailey et al. |
| 2006/0051814 A1 | 3/2006 | Jackowski et al. |
| 2007/0073195 A1 | 3/2007 | Chen |
| 2010/0033183 A1 | 2/2010 | Ochi et al. |
| 2011/0009749 A1 | 1/2011 | Zamboni |
| 2011/0026801 A1 | 2/2011 | Dohata et al. |

FOREIGN PATENT DOCUMENTS

| | | |
|---|---|---|
| JP | 4-332531 | 11/1992 |
| JP | 62-26052 | 8/1994 |
| JP | 08-050843 A | 2/1996 |
| WO | 97/17896 | 5/1997 |

OTHER PUBLICATIONS

Alperin et al., "Quantifying the effect of posture on intracranial physiology in humans by MRI flow studies", Journal of Magnetic Resonance Imaging 22:591-596 (2005).

Batzdorf et al (Chiari malformation and syringomyelia, 2008).

Bottomley et al., What is the Optimum Phased Array Coil Design for Cardiac and Torso Magnetic Resonance?, MRM 37:591-599, 1997.

Damadian et al., "The Possible Role of Cranio-Cervical Trauma and Abnormal CSF Hydrodynamics in the Generis of Multiple Sclerosis", Physiol. Chem. Phys. & Med. NMR (Sep. 20, 2011) 41: 1-17.

Duan et al. Three-dimensional CT study on normal anatomical features of atlanto-axial joints. 2007 Surg. Radiol. Anat. 29:83-88.

Feng, et al., A New Phased Array Spine Coil for Vertical Field MRI System, Proc. Intl. Soc. Mag. Reson. Med. 11, 2003.

Guclu et al., A method for Preamplifier-Decoupling Improvement in Quadrature Phased-Array Coils, Journal of Magnetic Resonance Imaging, 19:255-258, 2004.

Hill et al. The role of adjustable scout lines in advanced spinal imaging. 2012 Proc. of the N.A.S.S. 27th annual meeting The Spine Journal 12 p. 142S paper#P97.

Hofmann et al (Phase-Contrast MR Imaging of the Cervical CSF and Spinal Cord: Volumetric Motion Analysis in Patients with Chiari I Malformation. AJNR AM J Neuroradial 21:151-158, Jan. 2000).

Ibell, The Design and Modelling of 2D Phases Arrays for MRI, Oct. 2003, Thesis, The University of Queensland.

Jinkins et al., Upright, Weight-bearing, Dynamic-kinetic Magnetic Resonance Imaging of the Spine—Review of the First Clinical Results, 2003, J HK Coll. Radiol., 6:55-74.

Karhu et al. Kinematic magnetic resonance imaging of the upper cervical spine using a novel positioning device. 1999 SPINE 24:2046-2056.

Koller et al. Assessment of two measurement techniques of cervical spine and C1-C2 rotation in the outcome research of axis fractures 2010 SPINE 35:286-290.

U.S. Appl. No. 08/978,084, filed Nov. 25, 1997.

U.S. Appl. No. 09/718,946, filed Nov. 22, 2000.

U.S. Appl. No. 10/131,843, filed Apr. 25, 2002.

Roemer, et al., The NMR Phases Array, Nov. 1990, Magenetic Resonance in Medicine 16, 192-225.

Salem et al. In vivo three-dimensional kinematics of the cervical spine during maximal axial rotation. 2013 Manual therapy 18:339-344.

Three Dimensional Analysis of Spinal Deformities, M. D'Amico, et al., (Eds.), IOS Press, 1995, pp. 445-451.

U.S. Appl. No. 14/208,343, filed Mar. 13, 2014.

U.S. Appl. No. 14/209,279, filed Mar. 13, 2014.

Weis et al., Simulation of the influence of magnetic field inhomogeneity and distortion correction in MR imaging, vol. 8, No. 4, p. 483-489, 1990 (Abstract).

Zamboni et al (CSF dynamics and brain volume in multiple sclerosis are associated with extracranial venous flow anomalies: a pilot program), Apr. 2010.

Zamboni et al (Intracranial venous haemodynamics in multiple sclerosis, 2007).

Kowalski et al. Jul./Aug. 1987 Am. J. NeuroRadiol. 8:697-702.

Netto. Dec. 2006 BSc Thesis Mechanical Engineering, Edith Cowan University, Australia, 145 pages.

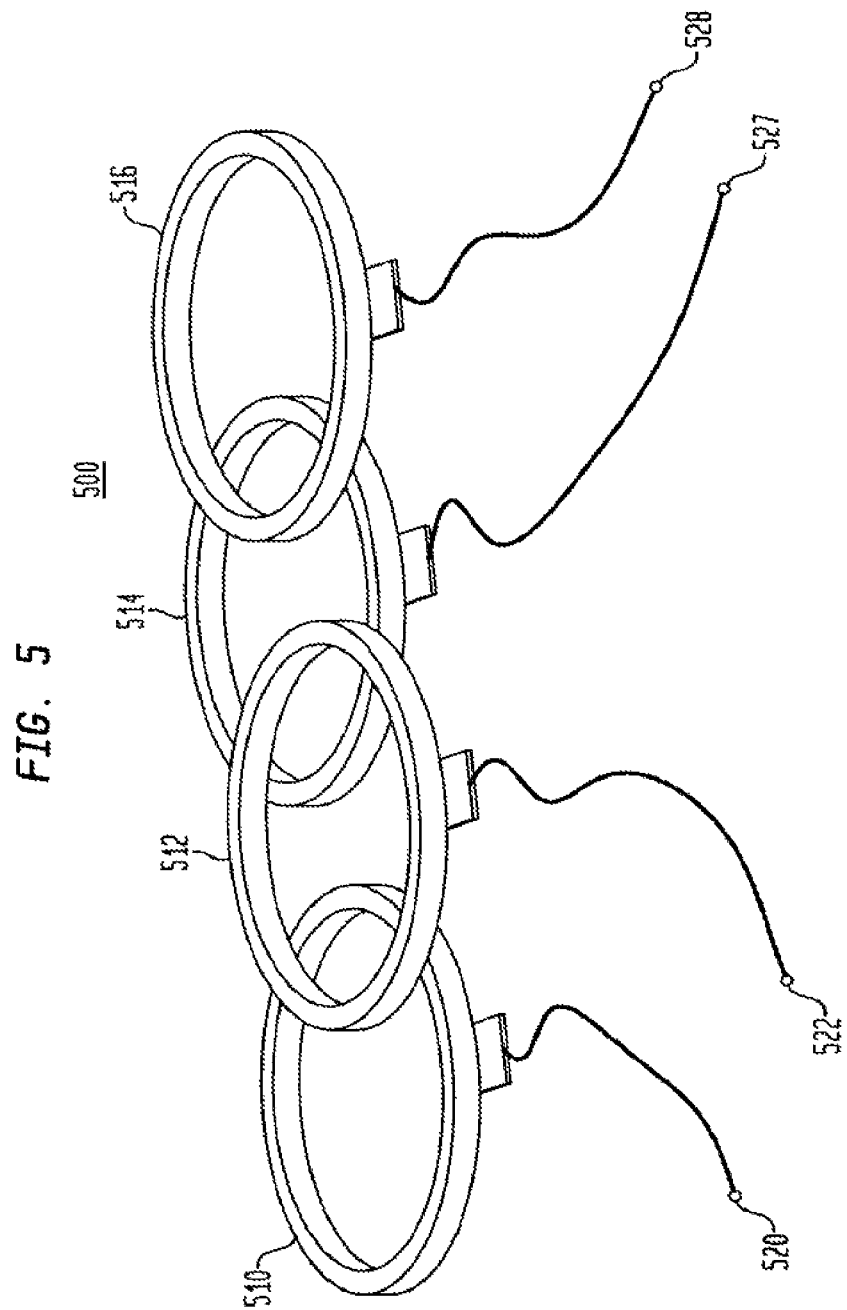

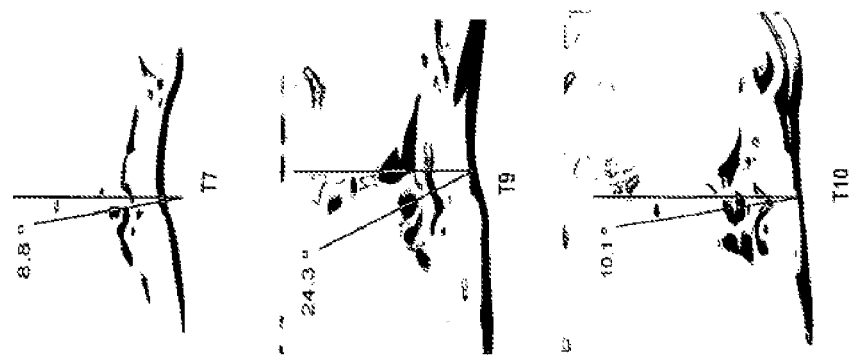
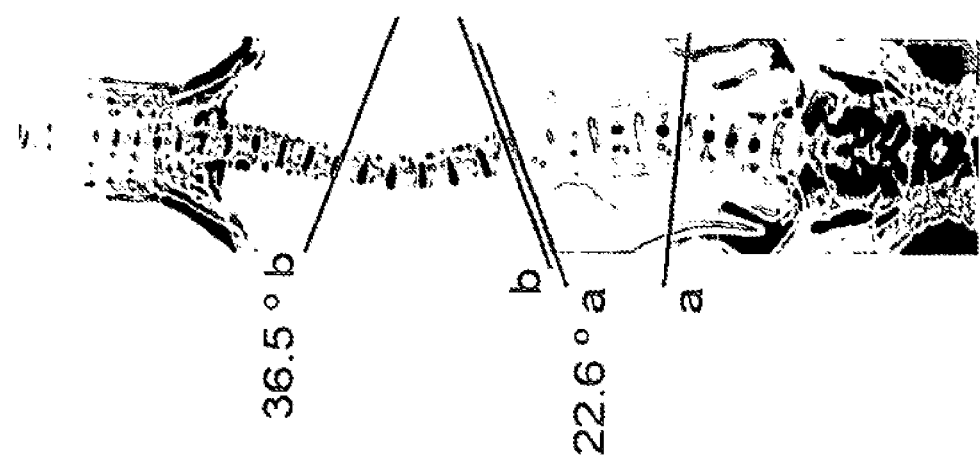

MAGNETIC RESONANCE IMAGING OF THE SPINE TO DETECT SCOLIOSIS

CROSS-REFERENCE TO RELATED APPLICATIONS

The present application is a divisional of U.S. patent application Ser. No. 12/152,139, filed May 12, 2008, which claims priority from U.S. Provisional Patent Application No. 60/928,545 filed May 10, 2007, the disclosure of which is hereby incorporated herein by reference.

BACKGROUND OF THE INVENTION

The present patent application relates to magnetic resonance imaging systems and methods for using such systems.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Despite the wide adoption of magnetic resonance imaging, X-ray detection continues to be the primary method used to detect certain abnormalities. One such abnormality is scoliosis. Scoliosis is an abnormal curvature of the spine. It occurs in approximately 2% of girls and 0.5% of boys. It is commonly diagnosed in early adolescents and may gradually progress as rapid growth occurs. Scoliosis patients typically undergo routine X-rays of the spine (typically two to three X-rays per year) throughout their adolescent growth spurt to monitor curvature progression so that corrective action may be taken. These repeated exposures, however, have been linked to an increase in breast cancer mortality among women.

In particular, researchers have found that women who were treated for scoliosis and exposed to multiple diagnostic X-rays during childhood and adolescence were at an increased risk of dying of breast cancer. Despite the reduction in X-ray exposure to the breast tissue of the women cited in the study the exposures used today are not insignificant. It is still recommended that efforts to reduce exposure continue and that repeated X-ray exposure should be minimized.

In that regard, although magnetic resonance imaging has been used to determine neurological complications due to scoliosis, its use has not been as widespread as possible. As mentioned above, using magnetic resonance imaging to diagnose and monitor scoliosis would remove a number of dangers associated with repeated exposure to X-ray radiation. First, X-ray radiation causes damage to living tissue. Second, MRI exams can be repeatedly done without health concerns. Third, X-rays do not provide the same level of image detail as can magnetic resonance imaging.

Nonetheless, magnetic resonance imaging has not replaced X-rays as the method of choice for monitoring scoliosis. Although magnetic resonance imaging of the spine has been performed, it has been generally done with the patient in a recumbent position. In the recumbent position, the spine is usually relaxed, which hinders monitoring and diagnosis of scoliosis. These magnetic resonance imaging procedures also tend to require a significant amount of time for each patient—as compared to X-rays. The long measurement time is primarily due to the time it takes to position the patient to obtain an image of the entire spine. This usually requires using different antennas to image different areas of the spine, which results in re-positioning the patient (including moving the bed in and out of the imaging volume).

Further in that regard, several factors impose significant physical constraints in the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the longitudinal or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. Pat. Nos. 6,414,490 and 6,677,753, the disclosures of which are incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the aforesaid applications, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

Another physical constraint on MRI imaging has been posed by the requirements for RF antennas to transmit the RF excitation energy and to receive the magnetic resonance signals from the patient. The antenna that receives the signals is positioned near that portion of the patient's body that is to be imaged so as to maximize the signal-to-noise ratio and improve reception of the weak magnetic resonance signals. The antenna that applies RF excitation energy can be positioned in a similar location to maximize efficiency of the applied RF energy. In some cases, the same antenna is used to apply RF excitation energy and to receive the magnetic resonance signals at different times during the process. However, it is often desirable to provide two separate antennas for this purpose.

The antennas are typically formed as one or more loops of electrically conductive material. Such a loop antenna must be positioned so that the conductor constituting the loop extends along an imaginary plane or surface having a normal vector transverse to the direction of the static magnetic field. Stated another way, the antenna must be arranged to transmit or receive electromagnetic fields in a direction perpendicular to the direction of the static magnetic field if it is to interact with the precessing atomic nuclei. This requirement has further limited available antenna configurations and techniques. For example, in a vertical-field magnet such as a ferromagnetic frame magnet having a vertical pole axis, it is impossible to use a loop antenna with the loop disposed generally in a horizontal plane below the body of a recumbent patient. Such an antenna has a normal vector which is vertical and hence parallel to the direction of the static magnetic field. A loop antenna which encircles the patient with its normal vector extending horizontally can be employed. Also, planar or saddle-shaped loops extending in generally vertical planes or surfaces, and having normal vectors in the horizontal direction transverse to the long axis of the patient can be positioned on opposite sides of the patient. However, these antenna configurations do not provide optimum signal-to-noise ratios in some procedures as, for example, in imaging the spine.

Of utility then are improved methods and systems for diagnosing and monitoring scoliosis using magnetic resonance imaging.

SUMMARY OF THE INVENTION

In one aspect the present invention is a method for detecting spinal abnormalities using magnet resonance imaging. The method comprises positioning a patient in an upright posture in an imaging volume of a magnet resonance imaging magnet with the spine of the patient adjacent to an antenna and capturing magnetic resonance imaging signals from a first portion of the patient's spine using the antenna with the patient positioned in a first position. The method may further comprise adjusting the patient position along a substantially vertical direction to a second position and capturing magnetic resonance imaging signals from a second portion of the patient's spine using the antenna with the patient positioned in the second position. Alternatively, multiple positions can be combined or if a large field of view is employed a single position of the patient may suffice.

In accordance with this aspect of the present invention, the first position preferably comprises positioning the patient such that the patient's lumbar vertebrae area is located in the imaging volume of the magnet.

Further in accordance with this aspect of the present invention, the second position preferably comprises positioning the patient such that the patient's cervical vertebrae area is located in the imaging volume of the magnet.

Further in accordance with this aspect of the present invention, capturing the magnetic resonance imaging signals comprises acquiring a three dimensional volume image of the first and second portions of the patient's spine. In addition, the method may further comprise generating a curved multi-planar reconstruction of the patient's spine from the captured imaging signals of the first and second portions of the spine.

Further in accordance with this aspect of the present invention, the method may desirably comprise generating a magnetic resonance image of spine from the base of the patient's skull to the patient's coccyx.

Further still in accordance with this aspect of the present invention, the method may further desirably comprise processing the captured imaged signals to measure the Cobb angle.

In yet another aspect, the method may comprise adjusting the patient position so that an upper portion of the patient's spine is moved from an approximate center of a first coil of the antenna to an approximate center of a second coil of the antenna. In some instances, this movement may be approximately 30-34 centimeters or more along a substantially vertical direction. In addition, in accordance with this method it is possible to complete the entire procedure in less than approximately ten minutes. Further, where the imaging volume is large enough, imaging may be done in a single position without moving the patient. For a small child, it may also be done in a single position.

In another aspect, the present invention comprises a magnet defining a patient-receiving space and having a static magnetic field with a field vector in a substantially horizontal direction; a patient support having a support surface for a human body, said patient support being positioned within said patient-receiving space and being pivotable about a horizontal pivot axis; and a planar housing having a first quadrature coil arrangement having a first butterfly coil and a first loop coil disposed above the first butterfly coil, a second quadrature coil arrangement having a second butterfly coil and a second loop coil disposed above the second butterfly coil, and a third loop coil arranged adjacent to and between the first and second loop coils. In yet another aspect, the present invention comprises a magnetic resonance imaging system that desirably includes a magnetic defining efficient—receiving space at having a static magnetic field with a field vector in a substantially horizontal direction, a patient support having a support service for a human body and a planar housing having phased array antenna coil assembly. The phase array antenna coil assembly preferably includes a first portion and a second portion, an active decoupling circuitry connecting to the first and second portions that is preferably offerable to selectively decoupled either the first or second portion from receiving magnetic resonance imaging signals.

Further in accordance with this aspect of the present invention, the patient's support is desirably positioned in the patient receiving space and is positioned about a horizontal pivot axis.

BRIEF DESCRIPTION OF THE DRAWINGS

FIG. 5 shows an antenna assembly in accordance with an aspect of the present invention.

FIGS. 6A, 6B and 6C show examples of images obtained in accordance with an aspect of the present invention.

DETAILED DESCRIPTION

Figure 1:
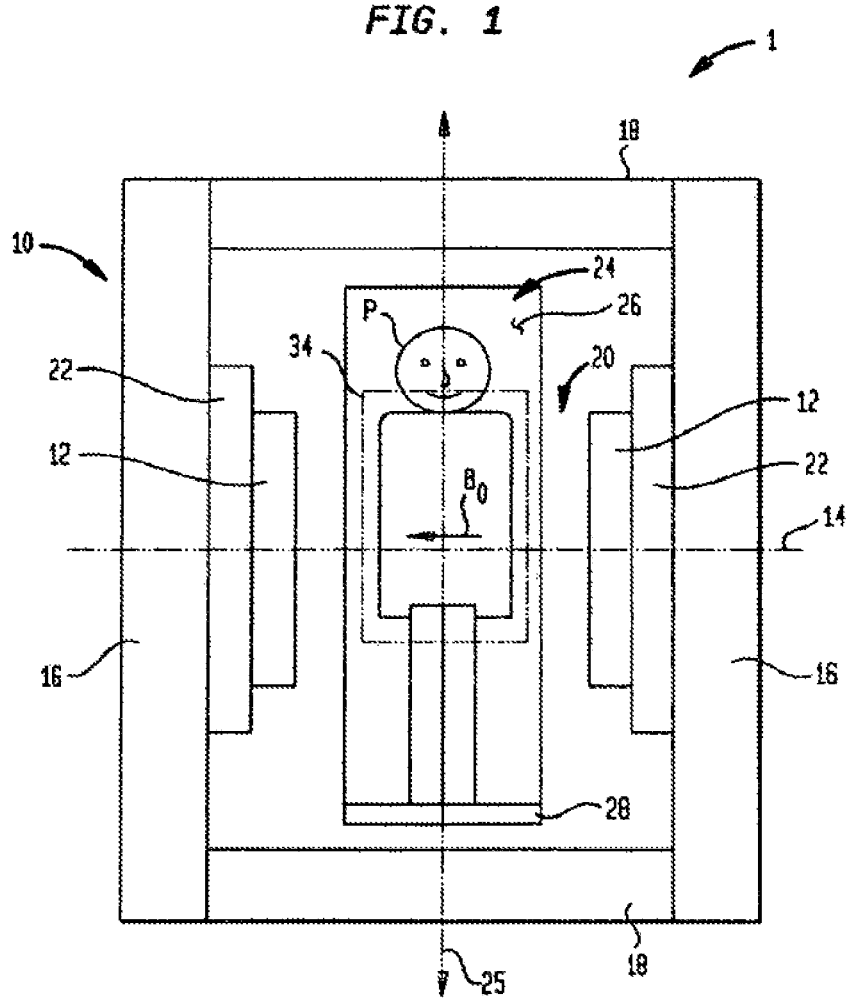
FIG. 1 illustratively depicts a front view of an apparatus in accordance with an aspect of the present invention.
Figure 2:
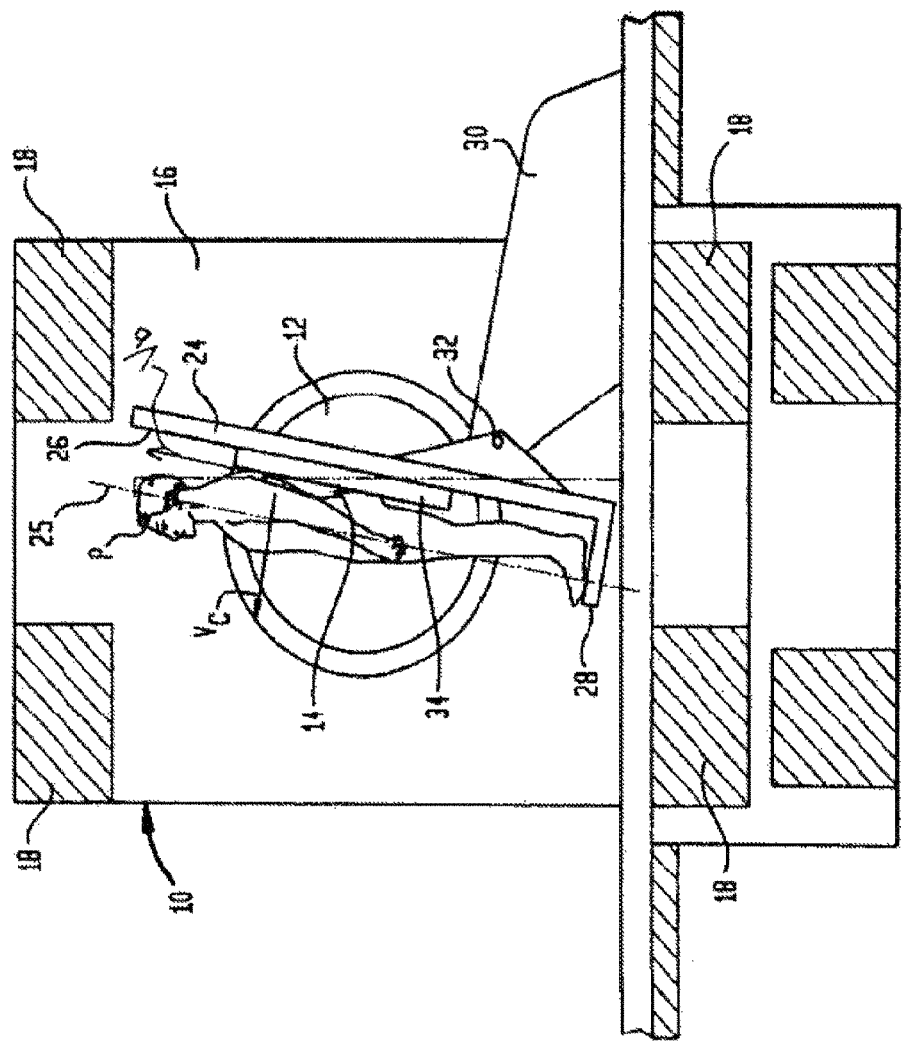
FIG. 2 is a side view of the apparatus of FIG. 1.

Turning to FIGS. 1 and 2, there is illustrated an apparatus 1 according to one embodiment of the present invention. The apparatus 1 includes a static field magnet having a frame 10 including a pair of poles 12 spaced apart from one another along a horizontal pole axis 14. Frame 10 further includes flux conducting and return members that, in the particular embodiment illustrated, include a pair of sidewalls 16 and columns 18 extending between the sidewalls 16. The particular frame depicted in FIGS. 1 and 2 is generally in accordance with the aforementioned U.S. Pat. No. 6,677,753, (hereinafter "the '753 patent"), although other configurations can be employed. The opposed poles define a patient-receiving space or gap 20 between them. The magnet further includes a source of magnetic flux adapted to direct into and out of the gap through poles 12 so as to form a static magnetic field having a field vector $B_0$ in the horizontal direction, parallel to pole axis 14. In the particular embodiment illustrated, the flux source includes a pair of electromagnet coils 22 encircling poles 12. These coils may be superconductive or resistive coils. Alternate flux sources such as coils disposed at other locations along the ferromagnetic frame and permanent magnets also may be employed.

Figure 3:
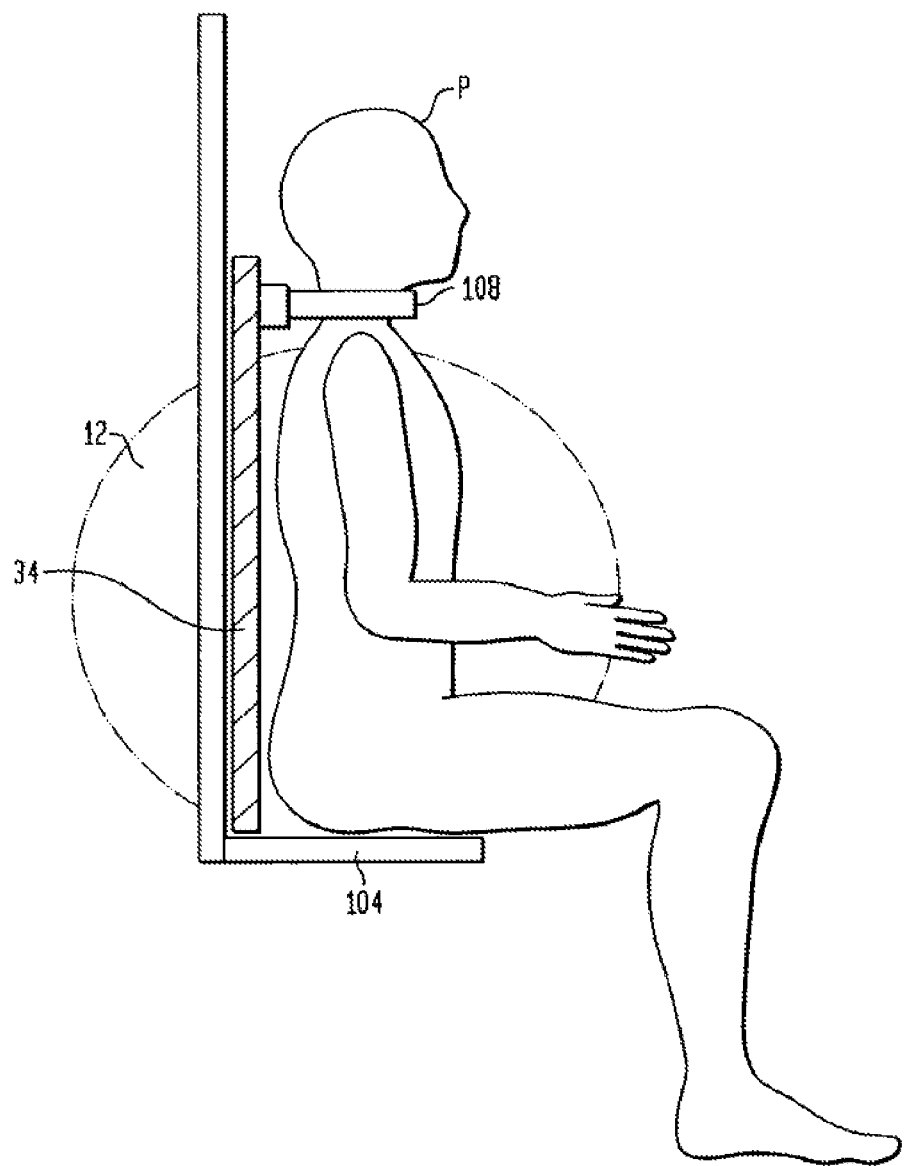
FIG. 3 is a side view of a patient and antenna assembly in accordance with an aspect of the present invention.

The apparatus further includes a patient support assembly including a bed 24 defining an elongated patient supporting surface 26 having a lengthwise axis 25 and a platform 28 projecting from the supporting surface at a foot end of the bed. In addition, as best seen in FIG. 3, a seat may be mounted to supporting surface 26 to allow a patient to be positioned in a sitting position. The patient supporting assembly further includes a frame 30. Bed 24 is pivotably mounted to the frame 30 for movement about a generally horizontal pivot axis 32. Pivot axis 32 is substantially parallel to pole axis 14. Bed 24 can pivot between an upright position in which the lengthwise direction over the bed extends generally vertically as seen in FIG. 2 and a fully horizontal position, in which the lengthwise direction of the bed 24 extends horizontally. As further described in the '753 patent, bed 24 also may be mounted for vertical motion relative to frame 30 and hence relative to the static field magnet 10. Moreover, frame 30 can be mounted for horizontal movement relative to the static field magnet. Appropriate actuators and control devices (not shown) are provided for moving the bed and for moving support frame 30.

Figure 4:
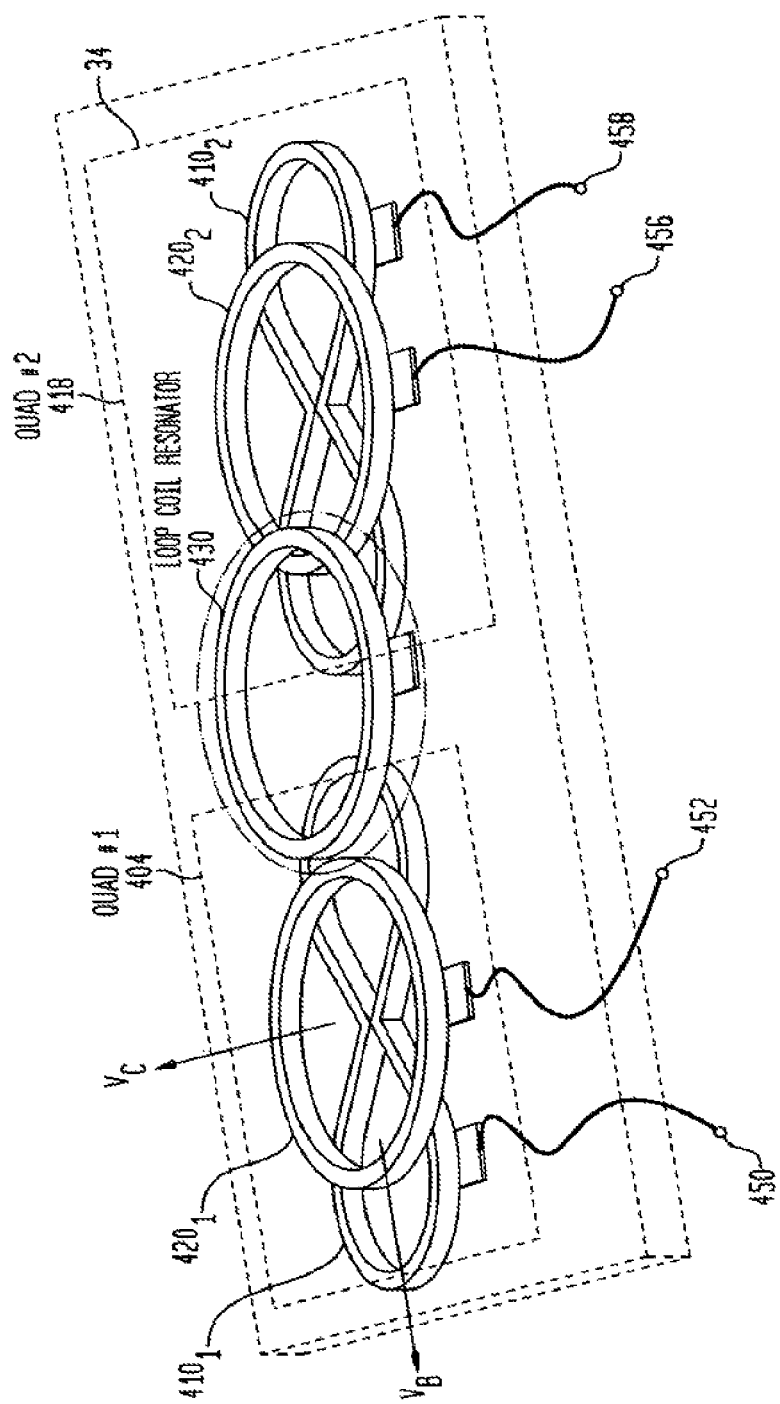
FIG. 4 shows an antenna assembly in accordance with an aspect of the present invention.

The patient support assembly further includes an antenna assembly schematically depicted as a planar box 34 in FIGS. 1, and 2. As best seen in FIGS. 4 and 5, the antenna assembly generally includes a plurality of coils, including coils having a winding extending in a loop configuration and others that extend in butterfly or "FIG. 8" configuration. Each configuration may be provided with a conventional coupling to a separate coaxial cable or other output line for conveying signals to a receiver or receiving signals from a transmitter. Also, each loop may include a capacitor (not shown) in series and/or in parallel with the conductor forming the loop so as to define a resonant antenna circuit.

The term "coil surface" as used herein refers to an imaginary surface defined by the central axis of the conductors constituting the coil or antenna. For example, as shown in FIG. 4, in the special case of a flat circular coil, the coil surface is the surface of the planar box 34. Each coil surface defines a coil vector $V_c$ normal to the coil surface itself (see FIGS. 2 and 4). In the case of a curved coil surface, the coil vector of the coil surface as a whole can be taken as the integral of the normal vector to the coil surface over the entire area of the coil surface inside the coil. In that regard, in some instances it may prove useful to have the surface of the box 34 contoured to more naturally match the shape of the human anatomy using some degree of curvature.

FIG. 5 shows a plurality of loop coils configured in a phased array arrangement. These coils may also be placed in planar box 34. In this configuration, the surface of the box may also be continued to match the shape of the human anatomy.

In the case of a substantially flat butterfly coil, each coil defines a coil vector $V_b$ is parallel to the surface in which the coil lies. As shown in FIGS. 2 and 4, these vectors are generally parallel to the surface of the planar box 34 in which the coils are disposed.

Returning to FIG. 3, there is shown an embodiment of the present invention for monitoring and detecting scoliosis in patients P. As shown, the patient P is positioned in the sitting position in the magnet apparatus 1 shown in FIGS. 1 and 2. In addition, although FIG. 3 shows a patient in a setting position, the patient may be positioned in a standing position as shown in FIGS. 1 and 2. As a general matter, the patient may be positioned in an upright position to take the MRI images needed for monitoring and detecting scoliosis. Thus, the descriptions of the sitting or standing position herein are meant to limit the present invention. Rather, the patient may be positioned in an upright position. With respect to FIG. 3 and for clarity, only those portions of the apparatus 1 needed to discuss this aspect of the invention is shown. Those include the pole 12, the antenna assembly 34 and a resonator 108. In accordance with a method aspect of the present invention, the patient P is first positioned on the seat 104 in an upright posture. Ideally, the patient is positioned so that the lower lumbar area coincides with the center of the imaging volume, i.e., the sweet spot of the magnet. In general, however, as long as the region of interest is located within the imaging volume, imaging may proceed. In this first position, the patient's lower lumbar area is then imaged.

In accordance with an aspect of the present invention, imaging is preferably done using a pulse sequence from which a three dimensional volume (3-D) volume image may be created. In addition, a pulse sequence lasting approximately three to four minutes may be used to obtain such images. Once imaging of the lower lumbar is completed, the patient is then lowered so that the upper part of the spine, i.e., the cervical spine, can be imaged. In this second position, as in imaging the lower spine, a pulse sequence from which 3D volume image can be reconstructed is preferably used. Likewise, imaging usually takes approximately three to four minutes to complete. Once both images are acquired and further processed they may be stitched together to form a full image of the spine as is illustrated in FIG. 6.

Patients with scoliosis usually receive posterior to anterior (P-A) radiography every four to nine months and an additional lateral disclosure once a year. The orthopedic surgeon now has to make a judgment as to the degree of rotation of the vertebra. Using the P-A radiographs the orthopedist measures the extent of the curvature in the scoliosis, i.e., the Cobb angle. These measurements are usually done by hand, e.g., drawings lines onto the X-ray images by hand and then measuring the Cobb angle.

As described above, using an upright MRI it is possible to complete a total examination in approximately 10 minutes. In this regard, examination includes data acquisition and patient positioning. Generally, it covers the time that the patient needs to be in the magnet. However, with complete automation even post-processing may take place contemporaneously with image acquisition. Therefore, the entire process may be completed in under 10 minutes. A total spine image in a standard solenoid MRI could take as much as 30 minutes and may under estimate the Cobb angle because the patient is in a supine posture. By keeping the exam time to a minimum the cost to the patient becomes competitive with radiography. In addition, with the patient in a standing or seated position, the results in the upright MRI are at least the same as with standard radiography.

In general, the MRI exam should be setup so that the patient just has to stand-up or sit down. All alignments could be preset for a typical person. A single spine coil (such as those shown in FIGS. 4 and 5) placed along the back of the patient P could cover the total range of interest. The MRI technician may first perform a quick scout scan to confirm the patient's position and align the MRI slices to be taken.

As discussed above, the preferred scanning technique is 3D volume acquisition. This would permit a doctor to do post-processing to produce views in the coronal (P-A radiograph), sagittal, or axial planes. The total spine could be scanned in two 3-D volume acquisitions. Each scan would take less than five minutes for a total scan time of ten minutes. The two scans could then be stitched together to form a single imaging volume set. Using a curved multi-planar reconstruction the doctor would produce an image of the spine in the coronal view. The image would show the spine from the base of the skull to the coccyx, as shown in FIG. 6. The images obtainable using this method also allow for better diagnosis. In addition, in accordance with another aspect of the present invention, the images obtained may be processed digitally to determine the Cobb angle. For example, a computer program may be written to detect the curvature in the spine and measure the Cobb angle automatically.

Returning to FIG. 3, as shown, a resonator 108 may be attached to the planar box 34 housing the antenna assembly. In this regard, the present invention may be done without attaching the resonator. The resonator 108, when attached, uses means that allows it to be adjusted to accommodate patients of different sizes. In addition, aside from improving the reception of the signals received, it also assists in immobilizing the patient. In the preferred embodiment, the resonator is not electrically connected to the other coil assemblies. Rather, it is inductively coupled to the other antenna assemblies in the box 34. Specifically, the resonator 108 is connected around the patient's neck to passively pick-up extra resonance signals when imaging the upper spine of the patient. In essence, the resonator 108 addresses the issue of having the cervical spine being positioned away from the coils in the upper part of the assembly 34. It detects the extra signals passively as is discussed in more detail in U.S. Pat. No. 5,583,438, which is assigned to the assignee of the present application, and the disclosure of which is incorporated by reference herein.

In one embodiment, the antenna assembly in the planar box 34 comprises the arrangement shown in FIG. 4. As shown, the antenna assembly 400 includes a pair of quadrature coils assemblies 404, 408. A quadrature coil antenna arrangement advantageously improves the signal-to-noise ratio by a factor up to $\sqrt{2}$. As a practical matter, the quadrature coil arrangement reduces the measurement or MRI scanning time by approximately one-half. That is, a measurement that takes approximately two minutes using a quadrature coil antenna arrangement will take approximately four minutes using another antenna arrangement. This improvement in performance translates into increased efficiency at MRI facilities.

Each assembly 404, 408 comprise a butterfly coil antenna $410_1$ and $410_2$ which are disposed beneath a loop coil antenna $420_1$ and $420_2$, respectively. Additional details regarding these types of antenna assemblies are discussed in U.S. patent application Ser. No. 10/998,395 entitled "COILS FOR HORIZONTAL FIELD MAGNETIC RESONANCE IMAGING," the disclosure of which is incorporated by reference herein, and included with this application as an attachment. In addition, a third loop coil 430 is shown arranged adjacent to and overlapping both quad coil assemblies 404, 408. The loop coil 430 acts as a passive resonator to each of these assemblies to pick up extra signals during image acquisition.

During image acquisition, an assembly 404, 408 may be selectively decoupled or turned off depending on the area of the spine being measured. For example, when the lower spine is being measured, quad assembly 404 (if positioned proximate the patient's cervical spine area) is decoupled from the magnetic circuit during imaging. This allows for better images to be acquired of the lower spine. Likewise, when imaging the cervical spine, the quad assembly proximate the lumbar spine area (e.g., quad assembly 408) is then decoupled from the circuit.

Figure 7:
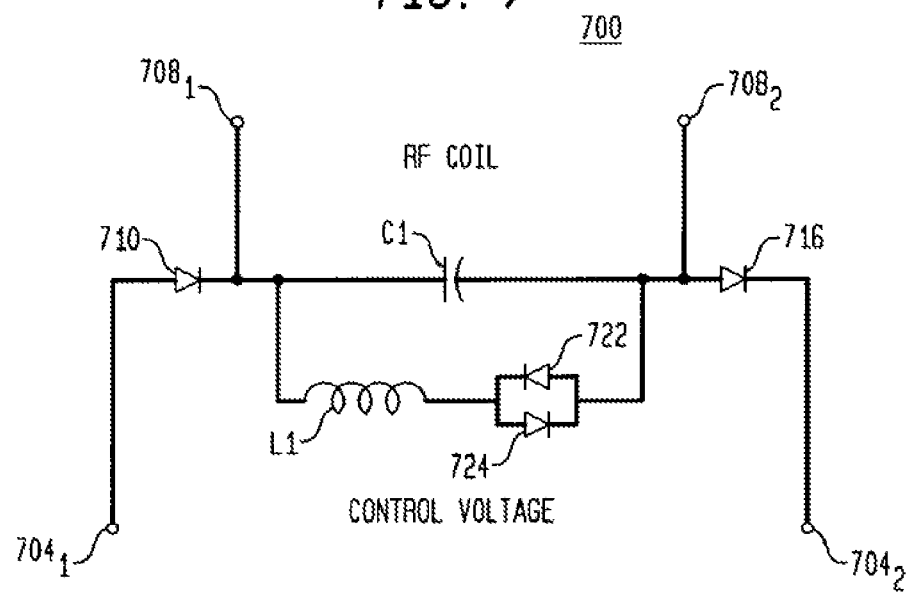
FIG. 7 is a schematic of a decoupling circuit in accordance with an aspect of the present invention.

Such decoupling may be accomplished using, for example, the circuit arrangement 700 shown in FIG. 7. As shown, the circuit 700 includes input ports $704_1$ and $704_2$ to which are applied a control voltage. The circuit 700 also includes output ports $708_1$ and $708_2$, which may be connected to a coil of the RF coil antenna assembly as shown in FIGS. 4 and 5. In the preferred embodiment, each quad coil 404, 408 is connected to a separate one of circuit 700. In particular, one coil is connected to nodes 450, 452, while the other is connected to nodes 456, 458. The phase array is now preferred.

As shown, a first diode 710 is connected to port $704_1$. A second diode 716 is connected to port $704_2$. Between the first and second diodes 710, 716 is a capacitor C1. In parallel with the capacitor C1 is an inductor L1, which is connected in series with pair of diodes 722, 724. During reception mode, a control voltage may be applied across the input ports $704_1$ and $704_2$. At a predetermined voltage, the diodes 710 and 716 will conduct and effectively detunes the capacitor C1. This, in turn, powers off the coil connected to the circuit 700.

Conversely, during transmission mode, the coil exerts a voltage across the diodes 722 and 724, thereby allowing the diodes 722 and 724 to conduct. In this way, during transmission mode capacitor C1 is not part of RF coil circuit. During reception mode diodes 722 and 724 do not conduct and C1 is part of the RF coil circuit.

According to one embodiment of the present invention, a decoupling circuit such as the circuit 700 may be connected to each coil in the RF coil antenna assembly. In this regard, different portions of the antenna may be selectively powered on and off. Thus, whereas a portion of the antenna that is positioned near a lower part of the spine may be powered on to receive images of the lower spine, a portion of the antenna near the upper spine may be powered off, and vice versa.

FIG. 5 shows an alternative antenna assembly 500 which may be operated in a similar manner to the double quad arrangement of FIG. 4. As those skilled in the art may recognize, this antenna 500 comprises a phased array assembly and functions as is known in the art. The antenna 500 includes a plurality of loop coils 510, 512, 514 and 516 arranged so that the coils 512 and 514 are arranged to overlap two of the other coils. Like antenna 400, this antenna 500 is effective in providing a wide field of view and high signal-to-noise ratio resonance signals. The antenna 500 is preferably coupled to the circuits shown in FIG. 7, one each at nodes 520, 522 and 526,528.

By using the antenna assemblies shown in FIGS. 4 and 5, imaging of the entire spine may take place using a single antenna assembly. This allows the process to take place by moving the patient in a substantially vertical direction without having to otherwise reposition the patient. For example, this avoids having to use two different antenna assemblies.

Turning now to FIG. 6, there is shown images of a spine of a patient having scoliosis that was acquired using the methods described above. FIG. 6A shows a representative slice of a 3-dimensional sagittal image acquisition of the spine from which multiplanar reconstruction of both coronal and axial views are generated, as shown in FIGS. 6B and 6C, respectively. FIG. 6B shows a coronal view of the spine showing Cobb angles measured to be 22.6 degrees and 36.5 degrees. FIG. 6C shows axial views of the spine showing direct measurement of vertebral rotations, for example 8.8 degrees at T7, 24.3 degrees at T9 and 10.1 degrees at T10. As shown in FIG. 6B, the Cobb angles was measured at 22.6 and 36.5 degrees. This measurement of the Cobb angle was done using software. As may be appreciated, these images allow for better diagnosis of the condition. In this regard, the Cobb angle may be seen and measured more easily.

In general, whereas in a radiograph, images of the spine are shadows in the presence of the other organs in the body, e.g., the ribs, heart, and other internal organs, MRI produces a single slice through the spine for all the MRI views: coronal, sagittal and axial. In FIG. 6 of the embodiment from a single 3D MRI exam all three views maybe obtained. The coronal view will indicate the severity of the scoliosis. The sagittal view will show the amount of Kyphosis and Lordosis in the spine. And, the axial views will indicate the severity of twisting in the spine and possible neurological complications of the scoliosis. Thus, MRI aids in making a better diagnosis and determining the severity of the scoliosis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A magnetic resonance imaging system, comprising:
   a magnet defining a patient-receiving space and having a static magnetic field with a field vector in a substantially horizontal direction;
   a patient support having a support surface for a human body, said patient support being positioned within said patient-receiving space and being pivotable about a horizontal pivot axis; and
   a planar housing having—
      a phased array antenna coil assembly including a first portion and a second portion, each portion operable to receive magnetic resonance image signals, wherein the first portion is aligned with an upper portion of the patient's spine including the base of the patient's skull and the second portion is aligned with a lower portion of the patient's spine including the patient's coccyx, such that the phased array antenna coil assembly extends in the lengthwise axis from the base of the patient's skull to the patient's coccyx, and wherein the length of the antenna assembly in the lengthwise axis is greater than the length of an imaging volume of the magnet, such that the phased array antenna coil assembly extends out of the imaging volume; and
      active decoupling circuitry connected to the first and second portions and operable to selectively decouple either the first or second portions from receiving magnetic resonance image signals; and
   a patient support adjustment mechanism for adjusting the patient support device between:
      a first upright position such that the upper portion of the patient's spine and the first portion are in the imaging volume of the magnetic resonance imaging magnet, and the second portion is out of the imaging volume, and
      a second upright position such that the lower portion of the patient's spine and the second portion are in the imaging volume of the magnetic resonance imaging magnet, and the first portion is out of the imaging volume.

2. The system of claim 1, further comprising active decoupling circuitry connected to the first and second portions of the phased array antenna coil assembly, the decoupling circuitry being operable to selectively decouple either the first or second portions from receiving magnetic resonance image signals.

3. The system of claim 2, wherein each portion of the phased array antenna coil assembly is connected to a separate decoupling circuit of the decoupling circuitry.

4. The system of claim 3, wherein each decoupling circuit comprises at least one diode and a capacitor, whereby activation of the at least one diode detunes the portion of the phased array antenna coil assembly connected to said decoupling circuit.

5. The system of claim 1, further comprising a resonator coil located proximate the housing.

6. The system of claim 1, wherein:
- the first portion comprises a first quadrature coil arrangement having a first butterfly coil and a first loop coil disposed above the first butterfly coil,
- the second portion comprises a second quadrature coil arrangement having a second butterfly coil and a second loop coil disposed above the second butterfly coil, and
- the phased array antenna coil assembly further comprises a third loop coil arranged adjacent to and between the first and second loop coils.

7. The system of claim 1, wherein each portion of the phased array antenna coil assembly is adapted to capture magnetic resonance images of the patient's spine.

8. The system of claim 7, wherein the magnetic resonance images of the patient's spine are three-dimensional volume images.

9. The system of claim 1, wherein images obtained in the first and second upright positions are capable of being stitched together to form a magnetic resonance image from the base of the patient's skull to the patient's coccyx, whereby scoliosis of the patient may be determined based on the stitched image.

\* \* \* \* \*